United States Patent
Ben-Haim et al.

(10) Patent No.: US 6,314,310 B1
(45) Date of Patent: *Nov. 6, 2001

(54) X-RAY GUIDED SURGICAL LOCATION SYSTEM WITH EXTENDED MAPPING VOLUME

(75) Inventors: Shlomo Ben-Haim, Haifa; Zeev Weinfeld, Herzliya; Assaf Govari, Kiriat Haim, all of (IL)

(73) Assignee: Biosense, Inc., New Brunswick, NJ (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/171,148
(22) PCT Filed: Jan. 22, 1998
(86) PCT No.: PCT/IL98/00034
§ 371 Date: Jan. 28, 1999
§ 102(e) Date: Jan. 28, 1999
(87) PCT Pub. No.: WO98/35720
PCT Pub. Date: Aug. 20, 1998

Related U.S. Application Data

(63) Continuation-in-part of application No. PCT/US97/02440, filed on Feb. 14, 1997.
(60) Provisional application No. 60/042,873, filed on Mar. 31, 1997.

(51) Int. Cl.[7] .................................................... A61B 6/00
(52) U.S. Cl. ........................... 600/424; 600/427; 606/130
(58) Field of Search .................................... 600/427, 424, 600/426, 425; 606/130; 378/42, 62, 20

(56) References Cited

U.S. PATENT DOCUMENTS

| | | |
|---|---|---|
| 3,644,825 | 2/1972 | Davis, Jr. et al. . |
| 4,017,858 | 4/1977 | Kuipers . |
| 4,317,078 | 2/1982 | Weed et al. . |
| 5,251,635 | 10/1993 | Dumoulin et al. . |
| 5,255,680 | 10/1993 | Darrow et al. . |

(List continued on next page.)

FOREIGN PATENT DOCUMENTS

| | | |
|---|---|---|
| 0728446A | 8/1996 | (EP) . |
| WO 94/06349 | 3/1994 | (WO) . |
| WO 95/07657 | 3/1995 | (WO) . |
| 9608209A | 3/1996 | (WO) . |
| WO 96/41119 | 12/1996 | (WO) . |
| WO 97/03609 | 6/1997 | (WO) . |
| WO 97/29709 | 8/1997 | (WO) . |
| WO 97/29710 | 8/1997 | (WO) . |

OTHER PUBLICATIONS

EPO Supplementary Search Report (Dated Mar. 14, 2001).

Primary Examiner—Marvin M. Lateef
Assistant Examiner—Shawna J Shaw
(74) Attorney, Agent, or Firm—Louis J. Capezzuto

(57) ABSTRACT

Apparatus for X-ray guided surgery, including a reference element (20), which is placed in contact with the body (32) of a subject. The element includes a plurality of fiducial marks (22a, 22b, 22c) and a first coordinate sensing device (24), in predetermined, fixed positions in the element (20). A surgical tool (36), having a distal end for insertion into the body (32), includes a second coordinate sensing device (40) fixed thereto. A fluoroscope (54) forms an X-ray image of the body, including the fiducial marks. A computer analyzes the image to determine the position of the reference element in the image, so as to find coordinates of the first coordinate sensing device relative to the image, and registers the position of the tool with the X-ray image by referring coordinates of the second coordinate sensing device to the known coordinates of the first position sensor.

28 Claims, 9 Drawing Sheets

U.S. PATENT DOCUMENTS

| | | |
|---|---|---|
| 5,265,610 | 11/1993 | Darrow et al. . |
| 5,309,913 | 5/1994 | Kormos et al. . |
| 5,383,454 | 1/1995 | Bucholz . |
| 5,515,853 | 5/1996 | Smith et al. . |
| 5,558,091 | 9/1996 | Acker et al. . |
| 5,566,673 | 10/1996 | Shiono et al. . |
| 5,577,502 | 11/1996 | Darrow et al. . |
| 5,638,819 | 6/1997 | Manwaring et al. . |
| 5,660,185 * | 8/1997 | Shmulewitz et al. ............... 128/749 |
| 5,662,111 | 9/1997 | Cosman . |
| 5,682,886 | 11/1997 | Delp et al. . |
| 5,715,822 | 2/1998 | Watkins et al. . |
| 5,740,222 * | 4/1998 | Fujita et al. ............................ 378/4 |
| 5,755,725 | 5/1998 | Druais . |
| 5,765,561 * | 6/1998 | Chen et al. ...................... 128/653.1 |
| 5,769,843 | 6/1998 | Abela et al. . |
| 5,772,594 | 6/1998 | Barrick . |
| 5,799,055 * | 8/1998 | Peshkin et al. ....................... 378/42 |
| 5,810,008 * | 9/1998 | Dekel et al. .................... 128/660.07 |
| 5,868,673 * | 2/1999 | Vesely . |
| 5,873,822 * | 2/1999 | Ferre et al. . |
| 5,954,647 * | 9/1999 | Bova et al. . |
| 6,076,008 * | 6/2000 | Bucholz . |
| 6,083,163 * | 7/2000 | Wegner et al. ..................... 600/429 |
| 6,122,541 * | 9/2000 | Cosman et al. . |
| 6,167,145 * | 12/2000 | Foley et al. ......................... 382/128 |

* cited by examiner

X-RAY GUIDED SURGICAL LOCATION SYSTEM WITH EXTENDED MAPPING VOLUME

RELATED APPLICATIONS

This application is a continuation-in-part of co-pending PCT Patent Application PCT/US97/02440 filed Feb. 14, 1997 and claims benefit of U.S. Provisional Patent Application 60/042,873 filed on Mar. 31, 1997. These applications are assigned to the assignee of the present patent application, and their disclosures are incorporated herein by reference.

FIELD OF THE INVENTION

The present invention relates generally to non-contact object location systems, and specifically to position tracking of medical probes.

BACKGROUND OF THE INVENTION

In recent years, minimally-invasive surgical techniques have become the preferred methods of performing many procedures that were previously carried out through an open incision. The adoption of these minimally-invasive techniques has gone hand-in-hand with the development of methods of visualizing the position of a surgical tool being manipulated inside the body. Although endoscopes offer a preferred mode of visualization in some areas of surgery, they are unsuitable for use in many procedures, such as neurosurgical and orthopedic procedures, in which tools must be inserted and manipulated very delicately in narrow spaces with poor optical visibility. In spinal surgery, for example, and in particular, in treatments of the intervertebral discs, a thin, hollow needle must be inserted near the center of the intervertebral space, in such a manner as to aspirate the fluid disc matter without touching the spinal cord, spinal nerves and blood vessels nearby.

In neurosurgery, before performing surgery, a three-dimensional image of the patient's head is formed, preferably using a CT imaging system. The image is used by the surgeon, as is known in the art, in planning the procedure and, preferably, in establishing a three-dimensional frame of reference for the operation, fixed with respect to the patient's anatomy. During the surgery itself, as the surgeon inserts and manipulates a surgical tool, its position is tracked in relation to the frame of reference. A stereotactic frame may be fastened to the patient's skin or bones, to be used in tracking and guiding the position of the needle.

Various methods are known in the art for tracking the position of a surgical tool with respect to the anatomy of a patient. For example, Medivision Advanced Support Systems, of Oberdorf, Switzerland, offers a system for spinal surgery that includes an optical position sensor fixed to a surgical tool and a reference element having three optical fiducial marks, in a fixed, predetermined spatial relationship. The reference element is fixed to the patient's back in a known position, and a camera is used to track the movement of the tool, relative to the reference element.

PCT patent publication WO 96/08209, whose disclosure is incorporated herein by reference, describes a combined position tracking and imaging system for use in medical applications, using a reference frame secured to a patient's head. The system monitors the position of a surgical instrument relative to the reference frame, using a mobile sensor, such as electromagnetic field sensor, as is known in the art, fixed to the instrument. Prerecorded images of the patient's body, generally CT images of the patient's head, are displayed responsive to the monitored position of the instrument relative to the body. The position of the instrument is registered on the prerecorded images.

Preferably, before the surgery, the frame is fixed to the patient's head, and a set of CT images is acquired. These images are used to register the position coordinates of the frame, including the coordinates of a reference position sensor therein, in relation to the patient's anatomy. Subsequently, during the surgery, signals output by the reference and mobile position sensors are monitored so as to track the coordinates of the sensors. The coordinates of the mobile sensor relative to the reference are used to register the position of the instrument with respect to the patient's anatomy, for example using the previously-acquired CT images.

Similarly, U.S. Pat. No. 5,383,454, whose disclosure is incorporated herein by reference, describes a position tracking and imaging system for use in neurosurgery. Before surgery, ultrasonic emitters are fixed to a number of reference points on the patient's head, and a set of CT images of the head are produced showing the positions of the reference points. Similar emitters are fixed to a surgical probe for insertion into the head. During surgery, an array of microphones in the operating room receive ultrasound signals emitted by the emitters on the patient's head and on the probe. These signals are used to determine the position and orientation of the probe relative to the reference points. The position and orientation information is used to display an image of the probe superimposed on the prerecorded CT images.

Position determination procedures are also described, for example, in U.S. Pat. Nos. 5,558,091, 5,391,199, 5,443,489 and 5,377,678, all of which are incorporated herein by reference. Position determining systems -generally use extrabody apparatus to locate a sensor attached to the surgical tool. The extrabody apparatus includes one or more field transducers, generally radiators or receivers, positioned above and/or around the patient, which transmit fields to and/or receive fields from the sensor. Each radiator or receiver has a characteristic "detection volume" in which the fields have sufficient strength in order to generate a strong enough signal in conjunction with the sensor, such that the location of the surgical tool can be determined to a desired level of accuracy.

The size of the detection volume is generally dependent on the size of the radiators or receivers. In some types of surgery, such as back surgery, the size of the detection volume may cause limitations on the surgery. If large radiators are used, they may interfere with the movements of a physician or other medical-staff member. Small radiators, which do not occupy much space, may not have a large enough detection volume and/or may have low resolution.

Although the position sensing system may be used to register the position of the tool with previously-acquired CT or MRI images, as described above, surgeons are generally unwilling to rely only on prerecorded images. In addition to the use of a reference frame or reference points and position sensors to track a surgical tool, as described in the above-mentioned PCT publication and in U.S. Pat. 5,383,454, for example, fluoroscopic X-ray imaging is generally also used to verify that the tool is indeed at the position indicated by the position sensors. This verification is needed, inter alia, to ensure that the frame has not shifted relative to the patient's anatomy, and that the position readings from the position sensors have not drifted. An error in the angle and depth of penetration of the tool can, clearly, have devastating consequences.

Typically, two-plane fluoroscopic X-ray imaging is used, wherein two perpendicular X-ray images are formed simultaneously, one an anterior-posterior image (top to bottom) and the other a lateral image (side to side). The two-plane fluoroscope is costly, however, and must be operated substantially continuously to monitor the position of the surgical tool resulting in undesirably high radiation dosages to the patient, as well as to the operating room staff. Furthermore, the fluoroscopic images acquired during surgery are not registered with the previously-acquired CT images or with the coordinates of the reference position sensor, so that there is no convenient way to re-calibrate the readings of the position sensors if they are found to be erroneous.

U.S. Pat. Nos. 5,265,610 and 5,577,502 suggest performing invasive medical procedures during which multiple X-ray images are periodically acquired, to give the operator information on the three-dimensional location of an invasive tool. In order to minimize the X-ray dosage to the patient, RF transmitters and receivers are used to receive positional information on the invasive tool. The positional information from the RF transmitters is used to superimpose the position of the tool on the X-ray images. The patient's motion may also be tracked, and the image display adjusted accordingly. Thus, it is maintained that the X-ray images may be updated less frequently than in conventional X-ray tracking systems.

SUMMARY OF THE INVENTION

It is an object of some aspects of the present invention to provide devices and methods for use in performing X-ray guided surgery with improved accuracy and convenience.

It is a further object of some aspects of the present invention to provide devices and methods useful in reducing radiation dosage to a patient during such surgery.

It is an additional object of some aspects of the present invention to provide devices and methods for registering coordinate readings received from a coordinate sensing device with an X-ray image during the course of a surgical procedure.

It is another object of some aspects of the present invention to provide apparatus and methods for tracking a medical probe within a patient using small field transducers, such as magnetic field radiators, which do not substantially obstruct access to the patient.

It is a further object of some aspects of the present invention to provide apparatus and methods for tracking a medical probe within a patient using small field transducers while maintaining a high signal-to-noise ratio.

It is another object of some aspects of the present invention to allow object tracking within a patient over an extended area, while maintaining high tracking accuracy.

In one aspect of the present invention, the surgery is guided using a single-plane X-ray image, without loss of three-dimensional position information.

In a further aspect of the present invention, the devices and methods are provided for use in spinal surgery, and in particular, for guiding a needle in the intervertebral space.

In accordance with these aspects of the present invention, a surgeon guides a surgical tool within the body of a patient by viewing an image indicating the position and orientation of the tool, superimposed on and registered with one or more fluoroscopic images of the body. The fluoroscopic images are captured as required during the surgery, preferably using a low-cost, single-plane fluoroscope. The fluoroscope is preferably rotated around the patient to capture and display multiple images from different angles, on which images the position and orientation of the tool are simultaneously registered. A costly two-plane fluoroscope, with its attendant high radiation dosage, is not required. The fluoroscopic images are captured and updated in real time, in the operating room, unlike CT images, which must typically be captured in advance, as described in the above-mentioned PCT publication WO 96/08209 and U.S. Pat. No. 5,383,454.

In some preferred embodiments of the present invention, a surgery system comprises a rigid, elongate tool, such as a needle, having a sharp distal end for insertion into the body of a patient, and a reference element, to be placed in contact with the body. The tool includes a coordinate sensing device, preferably adjacent the tool's proximal end. The reference element likewise includes a coordinate sensing device, preferably similar to that of the tool, and at least three X-ray fiducial marks, in known positions relative to the sensing device on the element. The fiducial marks are placed so as to fully define the position and orientation of the element, and thus of the sensing device thereon, in X-ray images thereof.

Preferably, each of the coordinate sensing devices on the tools and within the reference element comprises one or more coils, which generate electrical signals in response to an externally-applied magnetic field generated by one or more radiators, for example, as described in U.S. Pat. No. 5,391,199, whose disclosure is incorporated herein by reference. More preferably, each of the sensing devices comprises a plurality of magnetic field-responsive coils, as described in PCT patent publication number WO96/05768, which is also incorporated herein by reference. A biopsy needle to which such a position sensing device is attached is described in PCT patent application PCT/IL97/00058, which is incorporated herein by reference. The signals generated by the coils are processed, preferably, to determine six-dimensional position and orientation coordinates of both the tool and the reference element relative to a reference frame based on a common set of magnetic field radiators, preferably coils, positioned in proximity to the patient's body.

Alternatively, any other suitable type of coordinate sensing device may be used for this purpose, including sensors, known in the art, based on mechanical, electromagnetic, ultrasonic, and optical principles. In particular, sensors responsive to a DC magnetic field may be used, as described in U.S. Pat. No. 5,558,091, which is incorporated herein by reference.

In the context of the present patent application and in the claims, the term "coordinate sensing device" will be understood to refer to any suitable sensor that generates signals responsive to position and/or orientation thereof, which signals are processed to determined coordinates of an object to which the sensor is fixed. It will further be understood that although preferred embodiments are described herein with reference to coordinate sensing devices that provide both position and orientation information, the principles of the present invention may similarly be applied using suitable combinations of sensing devices that provide only position information or only orientation information. Furthermore, while preferred embodiments are described herein with reference to sensors on the tool and fixed to the patient, which measure fields from radiators adjacent to the body, the principles of the present invention may also be applied by placing field emitters on the tool and patient and using receivers adjacent to the body to receive the emitted fields.

In preferred embodiments of the present invention, the reference element is placed in contact with the patient's skin, adjacent to the area of the body into which the tool is to be inserted, and is preferably clamped or glued firmly in place. The position and orientation of the element, relative to anatomical features of interest in the patient's body, are ascertained by acquiring one or more X-ray images in one or more planes, and then determining the coordinates of the fiducial marks on the element in the one or more images. It will be appreciated that since the relative positions of the fiducial marks on the element are predetermined and known, the coordinates of the marks in even a single one of the images are sufficient to determine the scale of the X-ray image and the six-dimensions of position and orientation of the element relative to the patient's body.

Preferably, the images are input to an image processing computer, of any suitable type known in the art, which analyzes the images to identify and determine the positions of the marks. The computer then finds the scale of the image and the position and orientation of the element.

Further preferably, two fluoroscopic images are acquired in two respective, generally perpendicular planes, so as to verify the coordinate determination. Alternatively or additionally, a CT image or image set may be acquired for this purpose.

The coordinates of the fiducial marks thus determined are used to find image-based six-dimensional position and orientation coordinates of the sensing device on the element, based on the known position of the sensing device relative to the marks. These image-based coordinates of the sensing device are compared with the six-dimensional signal-based coordinates, determined from the signals that are generated by the sensing device itself, as described above, so as to register a signal-based coordinate system, associated with the coordinate sensing device, with an image-based coordinate system, associated with the X-ray images. Preferably, the computer displays the position of the element and the device thereon in one or more of the images.

Further preferably, the computer compares the distances between the positions of the fiducial marks in the X-ray images to the actual, known distances between the marks, and determines an image scaling factor based on the comparison.

Alternatively or additionally, a coordinate sensing device may also be provided on a fluoroscopic camera that is used to acquire the X-ray images, in addition to the coordinate sensing devices on the reference element and the surgical tool, as described above. Signals from the sensing device on the camera may be used in determining the image scaling factor, as well as in identifying the image view angle. The additional coordinate sensing device on the camera may obviate the need for the coordinate sensing devices on the reference element and the surgical tool to provide both position and orientation coordinates thereof When the tool is brought into the surgical field, its position and orientation coordinates are determined using the signals generated by the sensing device thereon. Preferably, three-dimensional position coordinates and two-dimensional angular azimuth and elevation coordinates of the tool are determined. (Generally, it is not necessary to known the tool's angle of roll, i.e., rotation about its own axis.) Alternatively, three-dimensional position coordinates of sensors at two points along the length of the tool may be determined and used to determine the tool's position and orientation.

The coordinates of the tool, determined in this manner, are registered with the X-ray images by reference to the calibrated coordinate readings generated by the sensing device on the reference element. The coordinates of the tool are then used to determine the position of the distal tip of the tool relative to the patient's anatomy based on the X-ray images. Preferably, the known coordinates and dimensions of the tool are also used by the computer to generate a properly scaled and oriented image of the tool, superimposed on one or more of the X-ray images.

During the surgery, as the tool is advanced into the patient's body, signals generated by the sensing device on the tool are used to track the tool's coordinates and, preferably, to update accordingly the display showing the image of the tool. Preferably, a new X-ray image is acquired from time to time, and the image is processed to find the coordinates of the fiducial marks on the reference element in the new image. More preferably, such a new image should be acquired and processed when the sensor-derived position or orientation coordinates of the element are observed to change, or at any other suitable time determined by a user of the system. The coordinates of the marks in the new image are compared with the previously-determined coordinates. If the coordinates of the marks are found to have changed, the sensorderived position and orientation coordinates of the element and the tool are re-registered with the new image, using the method described above. This procedure is used to correct for any translational or rotational motion within the surgical system, as well as for any changes of scale of the X-ray image that is acquired and displayed.

In some preferred embodiments of the present invention, the X-ray images acquired immediately before and/or during a surgical procedure are registered with previously-acquired CT images of the patient's body. Before acquiring the CT images, the reference element is fixed to the patient's body in a desired position, as described above, so that the fiducial marks on the element appear in the CT images. The reference element remains fixed to the body in this position during the surgical procedure. The image-derived coordinates of the fiducial marks in the X-ray images are compared with corresponding image-derived coordinates in the CT images, in order to register the X-ray and CT images.

Preferably, based on this image registration, the CT images are rotated and/or scaled, as is known in the art, so as to align the CT images with the X-ray images. Furthermore, three-dimensional CT image information, rotated and/or scaled in this manner, may be projected onto the plane of the X-ray image and superimposed on the X-ray image or displayed alongside it. Additionally or alternatively, the coordinates of the tool and/or an image of the tool may be displayed on an appropriate CT image.

In some preferred embodiments of the present invention, the tool is held in an adjustable guide, which aligns the long axis of the tool with a desired, linear course of penetration into the patient's body, for example, in one of the intervertebral spaces. The guide, as is known in the art, allows the tool to be advanced only along this linear course, although the course may be adjusted if necessary. The methods described above for determining and registering the position and orientation coordinates of the tool are used in adjusting the guide with respect to the desired course.

In other preferred embodiments of the present invention, the desired, linear course of penetration is marked by the user with reference to one or more of the X-ray images, for example, by entering into the computer coordinates of points along the course. Preferably, the computer marks the course on the image, and displays the position of the tool relative to the course. Further preferably, the computer sounds an alarm if the tool deviates from the course by more than a predetermined tolerance and/or presents a visual cue to indicate the correct direction in which the tool should be moved.

It will be appreciated that the above-described preferred embodiments of the present invention enable a surgeon to insert and manipulate a tool in a patient's body under the visual guidance of an X-ray image of the body that includes an accurate, continuously-updated representation of the tool. The X-ray image is acquired during the surgical procedure and may be updated as desired. In methods known in the art, by contrast, visual guidance is provided, if at all, using previously-acquired X-ray or CT images. Such images cannot show changes occurring within the patient's body. Furthermore, if registration or proper scaling of the previously-acquired images is disturbed, for example, by mechanical disalignment of elements of the system, the procedure must generally be interrupted in order to recalibrate.

Furthermore, the present invention may be practiced using ordinary fluoroscopy equipment that is already present in many operating rooms. The image and the coordinates of the tool are updated, as described above, with minimal interference with the surgical procedure and with other equipment present in the operating room, and with minimal radiation dosage to the patient. The present invention also allows the surgeon to view images of the patient's anatomy and the tool being inserted in two mutually-perpendicular image planes. Under methods known in the art, special dual-plane fluoroscopes, which are bulky, costly and expose the patient to greater radiation dosage, must normally be used for this purpose.

In accordance with another aspect of the present invention, surgery is performed using one or more miniature magnetic field transducers, preferably radiators, which are moveable with respect to the patient. Such miniature radiators generally do not interfere with the actions of the surgeon, and may be moved during surgery out of positions which interfere with the surgeon, without disrupting position determination.

In PCT patent application PCT/US97/02440, which is assigned to the assignee of the present application and whose disclosure is incorporated herein by reference, a radiator including one or more miniature field transducers is placed in proximity to a patient. The radiator is small and does not substantially obstruct access of a physician to the patient's body. However, the radiator has a small detection volume due to the miniature size of the transducers. Therefore, PCT/US97/02440 suggests using a moveable radiator which can be repositioned during surgery. One or more reference elements are attached to the patient's body. The reference elements are generally used to register the position of a surgical tool or probe with the body. In addition, when the radiator is moved, the reference elements are necessary in order to establish the position of the radiator with respect to the frame of reference of the patient's body.

In some preferred embodiments of the present invention, the method of the above-mentioned PCT application PCT/US97/02440 is improved to allow more accurate, quick and flexible use of the transducer radiators. A plurality of reference elements, preferably coupled with fiducial marks, are placed on the patient's body. The reference elements include miniature coordinate sensing devices, as described above. The fiducial marks allow the positions of the reference elements to be visualized in images taken of the body, as described above, including both CT images acquired before the surgical procedure and fluoroscopic X-ray images acquired during the procedure. The reference elements are placed on the body in a sufficient density such that for every desired position of the radiator relative to the body, at least one of the reference elements is situated within the detection volume of the radiator.

Preferably, the reference elements and fiducial marks are placed on a strap, which is laid along the patient's body. Preferably, the fiducial marks are mounted on the reference elements or are positioned at fixed points relative to the reference elements, so that it is easy to register the positions of the reference elements on images of the body.

Alternatively or additionally, the strap has sufficient rigidity to maintain a substantially fixed shape when placed on the body, and the reference elements are attached at fixed points relative to the strap. Three or more fiducial marks are attached to the strap at positions suitable to register the reference elements on an image taken of the body and reference elements.

During surgery, the radiators and/or the patient are moved as needed. Each time the position of the surgical tool is determined, the position of at least one of the reference elements is also determined, so as to register the position of the tool in a reference frame fixed to the body, by comparing the tool position determination to that of the reference elements. Due to the quick rate of position determination, the position tracking continues substantially uninterrupted even when the radiator is in movement.

Preferably, each time the radiators or patient are moved, and/or periodically, independent of the movements of the radiator, the signals from all the reference elements are compared to find the element which offers the strongest signal. The position of this reference element is determined and is used to register the position of the tool during position tracking. Preferably, the position of the tool derived in this manner is used to register an image of the tool, either on a fluoroscopic X-ray image, as described above, or on a previously-acquired image, such as from a CT or MRI scan.

In some preferred embodiments of the present invention, the detection volumes of the radiators are indicated on the images of the body, or in any other suitable manner. Preferably, the detection volume of each radiator is indicated separately. For example, each detection volume may be indicated by a different color, which is preferably also marked on the respective radiator itself. Preferably, the indication of the detection volume of each radiator is updated each time the radiator is moved. Further preferably, the surgeon may set a desired resolution level, and the detection volume is determined accordingly and indicated on the images.

Preferably, before surgery the position determining system is calibrated by sequentially determining the positions of the reference elements relative to the body. Preferably, an image of the body is produced which includes the reference elements attached to the body, for example, by CT, MRI or X-ray imaging, and the positions of the reference elements are registered on the image.

It will be appreciated that although preferred embodiments are described herein with reference to certain types of surgical procedures, for example, treatment of the intervertebral discs, the principles of the present invention may similarly be applied to procedures of other types, such as other orthopedic and neurosurgical procedures.

There is therefore provided in accordance with a preferred embodiment of the present invention a method for X-ray guided surgery, including: placing a reference element, to which a reference coordinate sensing device is fixed, on the body of a patient, acquiring an X-ray image of the body, including the element, during the surgery, processing the image to determine image-based coordinates of the reference coordinate sensing device, receiving and processing signals from the reference coordinate sensing device to determine signal-based coordinates thereof, and registering the image-based and signal-based coordinates to determine a coordinate transformation therebetween.

Preferably, registering the coordinates to determine a coordinate transformation includes determining an image scale factor.

Preferably, the method includes determining coordinates of an X-ray camera used to acquire the X-ray image, wherein determining the image scale factor includes comparing the camera coordinates to the coordinates of the reference coordinate sensing device.

Preferably, the method includes determining a view angle of the camera relative to the body, based on the coordinates of the camera.

Preferably, receiving and processing the signals from the reference coordinate sensing device to determine signal-based coordinates thereof includes determining six-dimensional position and orientation coordinates.

Preferably, the method includes bringing a surgical tool, to which a tool coordinate sensing device is fixed, into proximity with the body of the patient, receiving and processing signals from the tool coordinate sensing device to determine signal-based coordinates thereof, and determining image-based coordinates of the tool by applying the coordinate transformation to the signal-based coordinates of the tool coordinate sensing device.

Preferably, the method includes displaying the image and registering a representation of the tool thereon using the image-based coordinates of the tool.

Preferably, acquiring the X-ray image includes acquiring a plurality of images from different view angles with respect to the body, and wherein displaying the image and registering the representation of the tool therein includes registering a suitably-oriented representation of the tool in at least two of the plurality of images.

Preferably, the method includes designating image-based coordinates of a target point within the body, and determining and displaying a linear course along which the tool is to be advanced so as to reach the target point.

Preferably, the method includes designating image-based coordinates of a target point within the body and determining a linear course along which the tool is to be advanced to the target point.

Preferably, the method includes advancing the tool into the body and comparing coordinates of the tool to the linear course so as to detect a deviation of the tool from the course.

Preferably, the method includes providing an indication to a user of the tool when the deviation detected exceeds a predetermined tolerance.

Preferably, providing the indication to the user includes issuing an alarm.

Preferably, the method includes correcting the linear course responsive to the deviation.

Preferably, receiving and processing signals from the reference and tool coordinate sensing devices includes receiving and processing signals generated by the devices in response to a common magnetic field.

Preferably, processing the image to determine image-based coordinates of the reference position sensor includes finding the locations in the image of fiducial marks on the reference element.

Preferably, acquiring the X-ray image includes acquiring a sequence of images during the surgery, and wherein processing the image to determine image-based coordinates includes processing at least two images in the sequence to determine respective image-based coordinates based on each of the at least two images.

Preferably, the method includes acquiring a CT image of the body after placing the reference element on the body, and registering the CT image with the X-ray image by finding coordinates of the element in the CT and X-ray images.

There is further provided in accordance with a preferred embodiment of the present invention, a method of tracking an object within a body, including attaching a plurality of reference coordinate sensing devices to the body and at least one object coordinate sensing device to the object, registering the positions of the plurality of reference coordinate sensing devices in a frame of reference fixed to the body, selecting at least one of the plurality of reference coordinate sensing devices in proximity to the object, and receiving and processing signals from the at least one selected reference coordinate sensing device and the object coordinate sensing device to determine signal-based coordinates of the object and of the selected reference device so as to register the object coordinates relative to the body.

Preferably, attaching the plurality of reference devices includes attaching devices such that at substantially every point in an area of interest in or on the body, at least one device is within a predetermined range of the point.

Preferably, receiving the signals includes receiving signals responsive to the strength of a field transmitted by or incident on at least one field transducer in proximity to the body, and wherein the predetermined range is determined in accordance with a detection volume of the field transducer, within which volume the coordinates of the coordinate sensing devices can be determined to a desired degree of accuracy.

Preferably, the detection volume has a substantially smaller extent than the area of interest.

Preferably, attaching the plurality of reference devices includes attaching at least one strap comprising the plurality of sensing devices.

Preferably, attaching the at least one strap includes attaching a substantially rigid strap.

Preferably, selecting at least one of the reference devices includes determining which of the reference devices provides registration of the coordinates of the object to a desired degree of accuracy.

Preferably, receiving the signals includes receiving signals responsive to the strength of a field transmitted by or incident on a field transducer, and wherein determining which of the reference devices provides the registration to the desired degree of accuracy includes measuring the strength of the signals received from the at least one of the reference devices.

Preferably, selecting the at least one of the reference devices includes comparing the strengths of the signals received from two or more of the plurality of reference devices.

Preferably, selecting the at least one of the reference devices includes periodically repeating the step of selecting at least one of the reference devices.

Preferably, receiving the signals includes transmitting and receiving energy fields between at least one of the devices and a field transducer situated in proximity to the body.

Preferably, the method includes changing a relative disposition between the field transducer and the body, wherein selecting the at least one of the reference devices includes selecting responsive to changes in the relative disposition between the field transducer and the body.

Preferably, the object includes a surgical tool.

Preferably, registering the positions of the plurality of reference devices includes acquiring an image of the body including two or more of the plurality of reference coordinate sensing devices.

Preferably, registering the positions includes processing the image to determine image-based coordinates of the two or more of the devices.

Preferably, the method includes attaching a plurality of fiducial marks to the body at fixed points relative to the reference devices.

Preferably, determining the image-based coordinates of the reference devices includes registering the positions of the devices relative to image-based coordinates of the fiducial marks.

Preferably, receiving signals includes transmitting and receiving non-ionizing fields.

Preferably, the method includes displaying a map of areas which are included in the detection volume of the at least one field transducer.

Preferably, the method includes producing an image of the body and wherein displaying the map includes superimposing the map on the image.

There is further provided in accordance with a preferred embodiment of the present invention, a method of tracking an object within a body including placing at least one field transducer, having a detection volume, in a vicinity of the body, determining the position of the at least one field transducer, displaying a map showing the detection volume of the at least one field transducer relative to the body, and controlling the tracking of the object responsive to the map.

Preferably, controlling the tracking includes moving the at least one field transducer responsive to the map so as to optimize tracking of the object.

Preferably, determining the position of the at least one field transducer includes determining the position of the at least one field transducer relative to a reference device attached to the body.

Preferably, the method includes producing an image of the body, wherein displaying the map includes superimposing the map on the image.

Preferably, moving the at least one field transducer includes moving the field transducer such that the object is within the detection volume.

Preferably, placing the at least one field transducer includes placing a plurality of field transducers, and wherein displaying the map includes associating each field transducer with an area on the map included in its respective detection volume.

There is further provided in accordance with a preferred embodiment of the present invention, a reference sensor strap for registering position information, including a band attachable to a patient's body and a plurality of reference sensors mounted on the band.

Preferably, the strap includes a plurality of fiducial marks at fixed positions relative to the reference sensors.

There is further provided in accordance with a preferred embodiment of the present invention, a system for determining the disposition of an object within a body of a patient, including a position sensor, which is coupled to the object, a plurality of reference sensors, which are attached to the body, a movable field transducer, which transmits fields to or receives fields from the position sensor and reference sensors; and a processor, which selects at least one of the reference sensors in proximity to the object and determines coordinates of the position sensor relative to the selected reference sensor, irrespective of movement of the field transducer relative to the patient.

Preferably, the field transducer includes a radiator.

Preferably, the field transducer includes a small transducer which does not substantially obstruct movements of a surgeon.

Preferably, the position sensor and reference sensors include magnetic field sensors.

Preferably, the system includes a strap which includes the reference sensors.

Preferably, the processor periodically selects the at least one reference sensor so as to allow accurate determination of the position of the object relative to the selected reference sensor.

Preferably, the processor selects the at least one reference sensor by transmitting fields which generate signals in the sensors, and comparing the strengths of the signals in the sensors.

Preferably, the system includes an imaging device for producing an image on which the determined coordinates are registered.

Preferably, the processor indicates a detection volume of the field transducer on the image.

Preferably, the object includes a surgical tool.

There is further provided in accordance with a preferred embodiment of the present invention, a system for determining the disposition of an object within a body of a patient, including a position sensor for coupling to the object, at least one reference sensor for attaching to the body, one or more field transducers having respective detection volumes for transmitting fields to or receiving fields from the position sensor and reference sensor, and a processor, which determines the disposition of the object and the positions of the field transducers responsive to the transmitted fields and indicates the detection volumes of the field transducers responsive to the positions.

Preferably, the processor displays a map of the detection volumes.

Preferably, the map is superimposed on an image of the body.

There is further provided in accordance with a preferred embodiment of the present invention, apparatus for X-ray guided surgery, including a reference element, which is placed in contact with the body of a subject, said element comprising a reference coordinate sensing device, in a predetermined, fixed position thereon, a fluoroscope, for forming at least one X-ray image of the body, including the reference element, and a computer, which receives signals from the reference coordinate sensing devices and processes the signals to determine signal-based coordinates thereof, and which analyzes the image to derive an image-based coordinate system and to find a transformation to register the signal-based coordinates and the imagebased coordinate system.

Preferably, the reference element includes a plurality of fiducial marks in predetermined, fixed positions thereon, and wherein the computer analyzes the image to find image-based coordinates of the marks, so as to derive the image-based coordinate system.

Preferably, the apparatus includes a surgical tool, having a distal end for insertion into the body, and including a tool coordinate sensing device fixed to the tool, wherein the computer receives signals from the tool coordinate sensing device and applies the transformation to the signals to determine image-based coordinates of the surgical tool.

Preferably, the apparatus includes a display, driven by the computer, on which display the at least one X-ray image is shown with a representation of the tool superimposed thereupon, wherein the representation is registered with the image based on the image-based coordinates of the tool.

Preferably, the apparatus includes a frame, which guides the tool along a predetermined path into the body, wherein the frame is adjusted in response to variations in the image-based coordinates of the tool.

Preferably, the at least one X-ray image includes a plurality of X-ray images, formed by the fluoroscope from at least two different angles with respect to the body.

Preferably, the apparatus includes a coordinate sensing device fixed to the fluoroscope, for determining the position of the fluoroscope relative to the body.

Preferably, at least one of the coordinate sensing devices includes a coil, which generates signals responsive to an externally applied magnetic field.

Preferably, the at least one coordinate sensing device includes a plurality of non-concentric coils.

Preferably, the apparatus includes one or more magnetic field generators, which apply magnetic fields to the coils.

The present invention will be more fully understood from the following detailed description of the preferred embodiments thereof, taken together with the drawings, in which:

DETAILED DESCRIPTION OF PREFERRED EMBODIMENTS

Figure 1A:
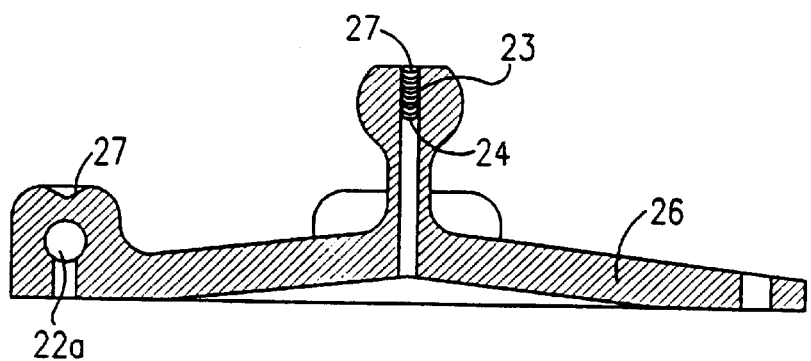
FIG. 1A is a schematic side view of a surgical reference element, including fiducial marks and a sensing device, in accordance with a preferred embodiment of the present invention.
Figure 1B:
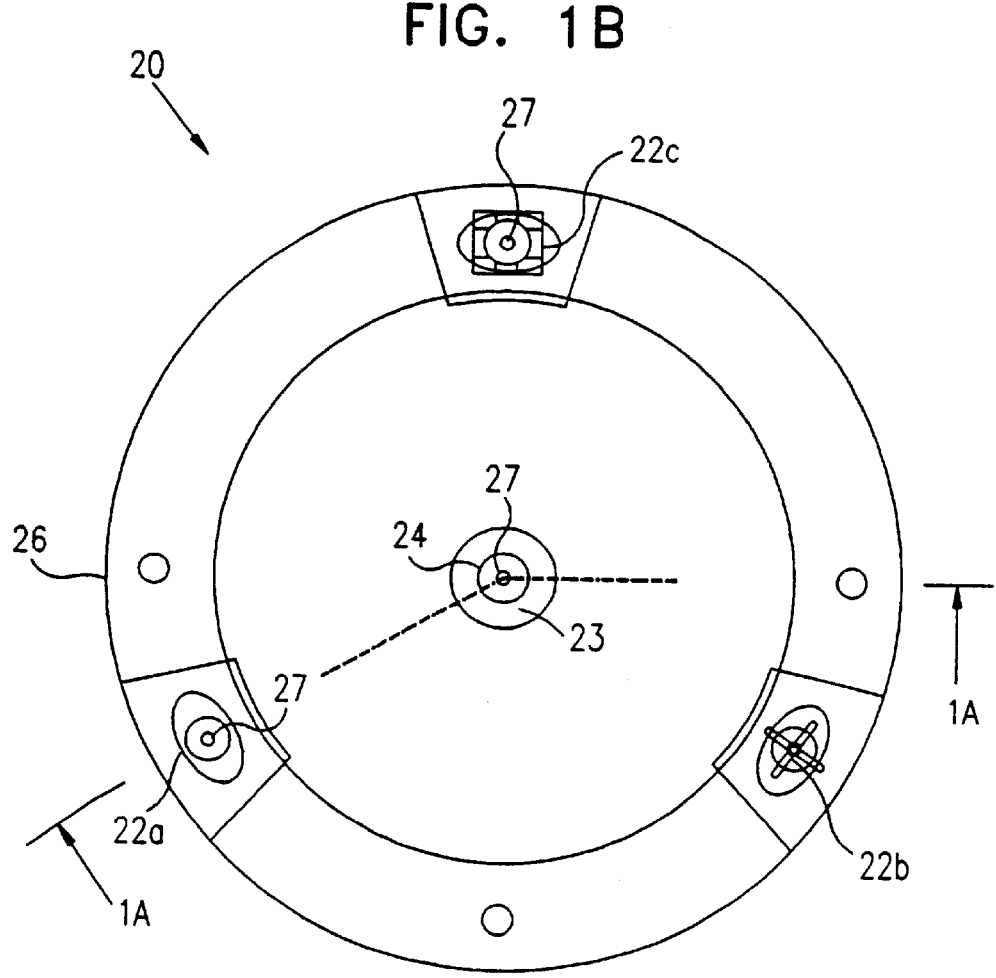
FIG. 1B is a schematic top view of the element shown in FIG. 1A.

Reference is now made to FIGS. 1A and 1B, which schematically illustrate a reference element 20, in top and side views, respectively, in accordance with a preferred embodiment of the present invention. Element 20 preferably comprises a disc of plastic material 26, which is most preferably transparent to both visible light and X-rays. A plurality of metal fiducial marks 22a, 22b and 22c, as are known in the art, are embedded in disc 26. A position and orientation sensing device 24, with an additional fiducial mark 23 on or adjacent to the sensing device, is similarly embedded in or fastened to element 20. Preferably, device 24 is fabricated so that a portion of the device, for example, a coil as will be described below, can itself serve as mark 23. The positions of fiducial marks 22a, 22b, 22c and 23 and of device 24 on element 20, and thus the distances between each pair of marks and between each mark and device 24, are predetermined and known.

Preferably, device 24 comprises a plurality of non-concentric sensor coils, as described in PCT patent publication number WO96/05768, and incorporated herein by reference. The coils generate signals in response to an externally-applied magnetic field, as will be described below. These signals are processed to determine six-dimensional position and orientation coordinates of device 24 and hence of element 20 to which the device is fixed.

Alternatively, device 24 may comprise any suitable type of position sensor known in the art, so long as it can be used to determine the six-dimensional coordinates of element 20 with sufficient accuracy for use in surgery, as will be described below.

As shown in FIGS. 1A and 1B, element 20 includes three fiducial marks 22a, 22b, and 22c, along with additional mark 23, although any suitable number of marks may be used. The fiducial marks have individual shapes or other features, differing one from another, so that each of the marks may be easily individually identified. Preferably, element 20 includes at least three marks, so as to fully define a coordinate system wherein, for example, the marks define the X–Y plane and an origin and distance scale therein. Further preferably, element 20 has indentations 27 adjacent each of marks 22 and 23. Indentations 27 are sized to receive the end of a tool having a position sensor thereon, for example, needle 36, as will be described below, so that the position sensor on the tool can be calibrated with respect to the positions of marks 22 and 23.

Although element 20 is conveniently made in a disc shape as shown in FIGS. 1A and 1B, any suitably-shaped element may be used. Preferably element 20 should conform to and/or be easily fixed to a part of the body of a patient against which it is to be placed.

Figure 2:
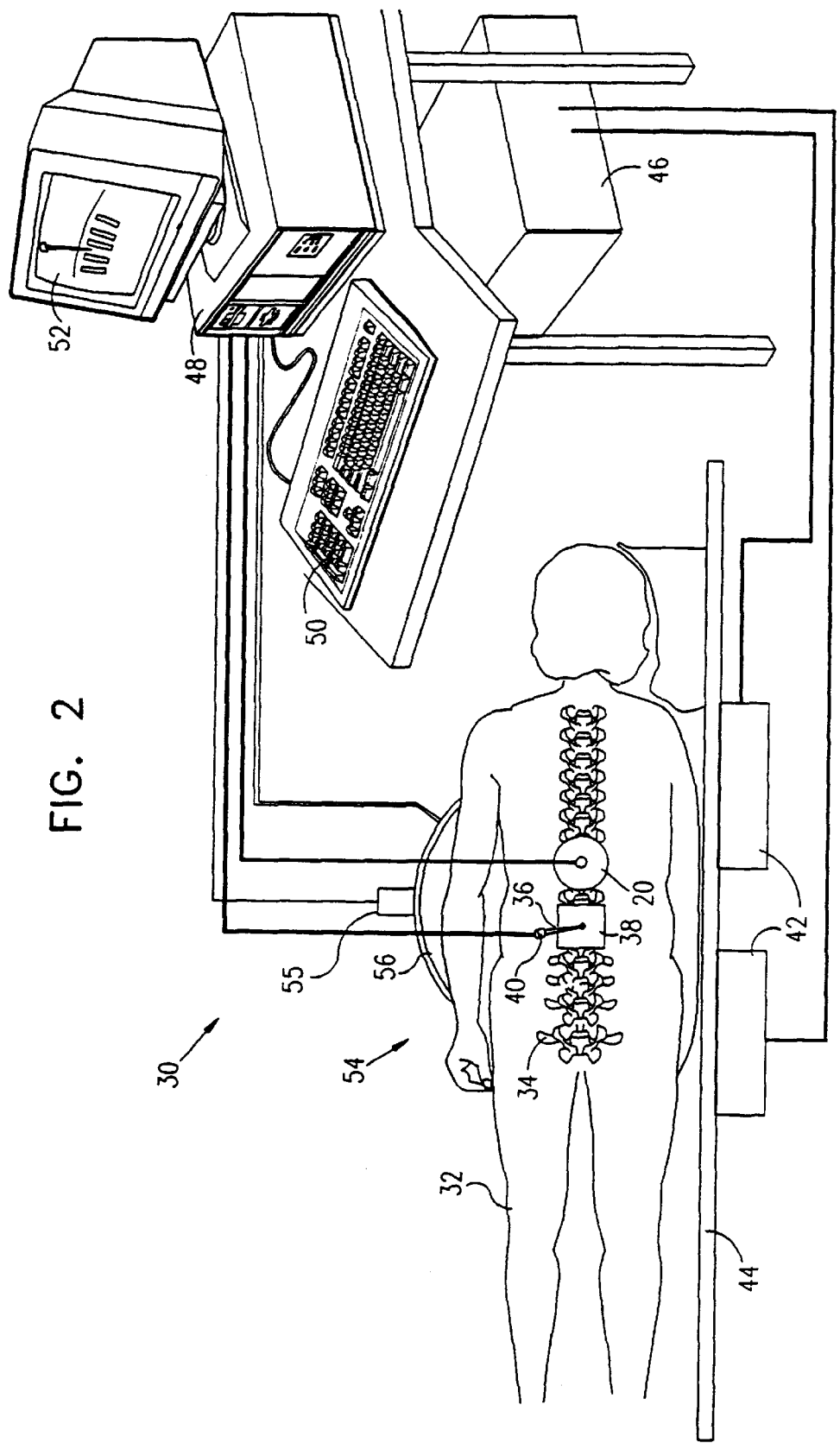
FIG. 2 is a schematic illustration of a surgical system, including the element of FIG. 1, in accordance with a preferred embodiment of the present invention.

Reference is now made to FIG. 2, which illustrates the use of element 20 as part of a system 30 for spinal surgery, in accordance with a preferred embodiment of the present invention. Element 20 is fixed to the back of a patient 32, preferably by gluing the element to the patient's skin. The element is placed adjacent to an intervertebral space 34 in the patient's back into which a needle 36 is to be inserted, for example, for the purpose of aspirating a ruptured disc, but not in such a position as to interfere with access of the needle to the space. Preferably needle 36 is held by a needle guide 38, known in the art, which enables the point at which the distal end of needle 36 is to penetrate the skin and the angle of its penetration to be precisely set and maintained.

A position and orientation sensing device 40, similar to device 24 on element 20, is fixed to the proximal end of needle 36. Magnetic field generator coils 42 are placed on or adjacent to a bed 44 on which patient 32 is lying. Field generator coils 42 generate time-varying magnetic fields at different frequencies, under the control driver circuitry 46, as described in the above-mentioned PCT publication. These fields cause the sensor coils in devices 24 and 40 to generate electrical signals, responsive to the devices' respective positions and orientations relative to coils 42. These signals are received by a computer 48, which analyzes them to determine relative six-dimensional position and orientation coordinates of devices 24 and 40, with respect to a common frame of reference, defined by field generator coils 42.

Alternatively, needle 36 may include one or more sensor coils, preferably of the type described in the above-mentioned U.S. Pat. No. 5,391,199, fixed along the length of the needle. For example, the needle may have two such coils at predetermined, mutually-spaced locations. Signals generated by these sensor coils in response to the magnetic field are analyzed by the computer to determine three-dimensional position coordinates of each of the sensor coils. The position coordinates of the two sensor coils are taken together to determine three-dimensional position and two-dimensional angular azimuth and elevation coordinates of needle 36 with respect to the frame of reference defined by field generator coils 42. It is generally not necessary to know the needle's roll angle (rotation about its own axis).

Preferably, computer 48 controls multiple aspects of system 30, including driver circuitry 46, and performs image processing functions, as will be described below. The computer preferably also receives input from user interface controls 50 and a drives a display 52, and may be coupled to a printer, disk drive and other suitable peripheral devices known in the art.

System 30 further includes a fluoroscope 54, as is known in the art, comprising an X-ray tube, which irradiates patient 32 from one side of his body, and an image intensifier/camera 56 on the opposite side. Any of a wide variety of existing fluoroscopes may be used for this purpose. Fluoroscope 54 need not be specially adapted for use in the framework of system 30, except that a video signal or other suitable image signal output is connected to computer 48. The X-ray tube is not shown in FIG. 2, since it is forward of the plane of the picture. Preferably, the tube and intensifier 56 may be placed at any convenient positions relative to patient 32, for example, with the tube below and the screen above the patient, so as to capture fluoroscopic images from any desired angle. These images are displayed by display 52 either one at a time or in split-screen or multi-screen combination, as will be described below. Optionally, an additional coordinate sensing device 55 is fixed to fluoroscope 54 and is coupled to computer 48, for determining the distance and/or view angle of the fluoroscope relative to reference element 20 and patient 32.

Figure 3:
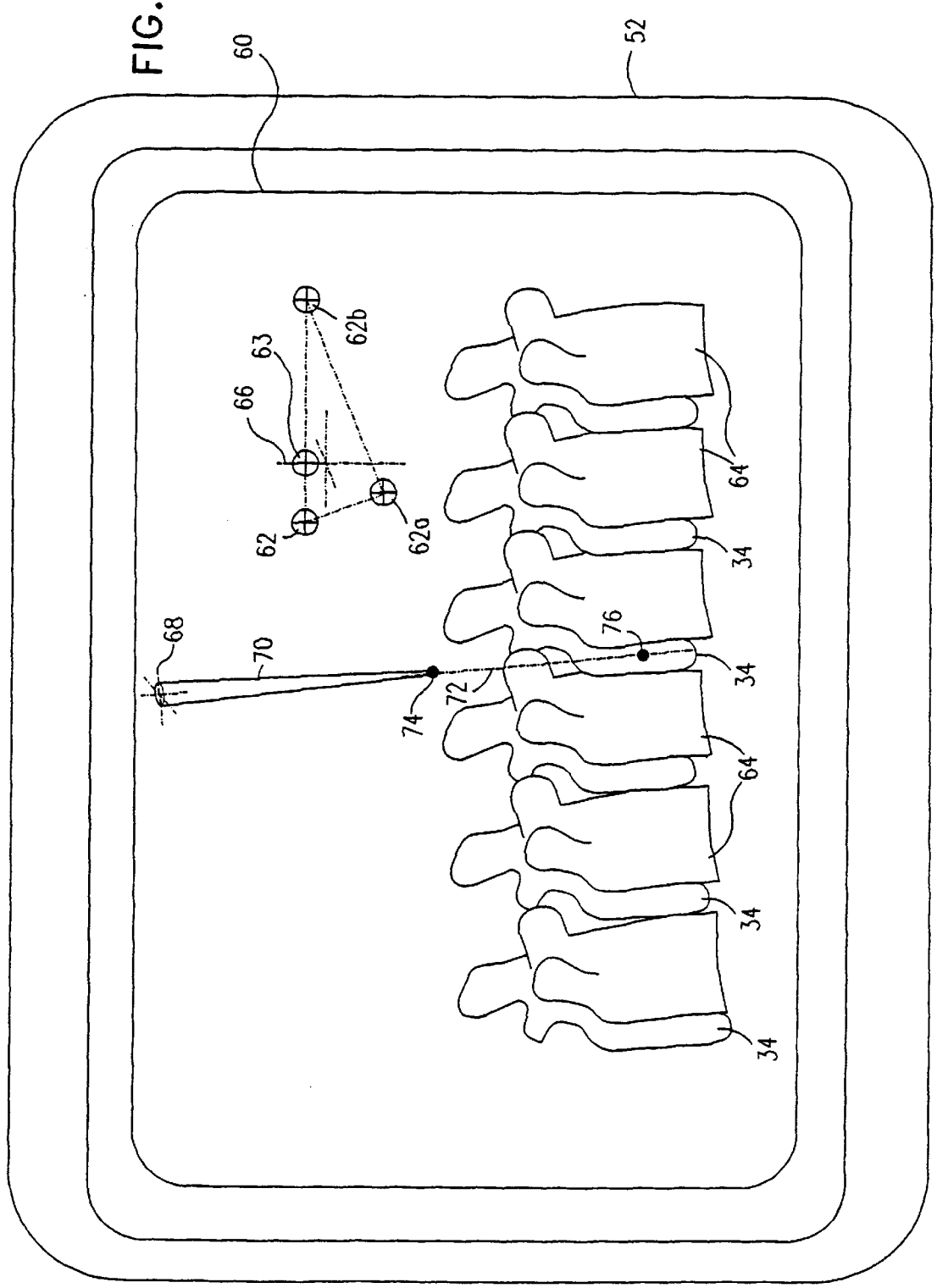
FIG. 3 is a schematic representation of a lateral X-ray image, including elements of the system of FIG. 2, in accordance with a preferred embodiment of the present invention.

FIG. 3 is a schematic illustration of a lateral fluoroscopic image 60, as displayed by display 52 following processing by computer 48. Image 60 includes vertebrae 64, along with reference points 62a, 62b, 62c and 63, corresponding respectively to fiducial marks 22a, 22b, 22c and 23 on element 20, whose general position is indicated by the dashed line connecting points 62a, 62b and 62c. Two-dimensional coordinates of points 62a, 62b, 62c and 63 in image 60 are determined, using image processing methods known in the art, and are used to determine the location and angular orientation of element 20. The relative coordinates of these points are compared with the known positions of marks 22 on element 20 to find a scaling factor for image 60 and to locate the six-dimensional image-based coordinates of device 24. Device 24 is not itself shown in FIG. 3, but its coordinates are indicated by pseudo-three-dimensional axes 66.

The image-based coordinates of device 24 are compared with the six-dimensional coordinates of the device as determined by computer 48 based on the magnetic-field-responsive signals generated by the device. A coordinate transformation, for example, a transformation matrix, is determined so as to register the signal-based coordinates with the image-based coordinates and to transform the coordinates from one coordinate system to the other. Normally, element 20 does not move during a surgical procedure, so that the signal- and image-based coordinates will remain in registration. The transformation is applied to transform the signal-based coordinates of device 40 on needle 36 (shown in FIG. 2) with image 60. The coordinates of device 40 are indicated by axes 68 in image 60, as shown in FIG. 3. If desired, an additional position sensor can be fixed directly to patient 32, to verify, if necessary, that the registration of the coordinates has not changed.

Preferably, computer 48 superimposes on image 60 a computer-generated representation 70 of needle 36 or, alternatively, a representation or cursor mark indicative only of the tip of the needle. Representation 70 will accurately portray needle 36 within image 60, since the representation is positioned, oriented and scaled in the image in accordance with the known coordinate transformation, determined as described above. As needle 36 is advanced into intervertebral space 34, computer 48 continually receives signals from device 40 and updates its determination of the signal-based coordinates of the device. This determination is used to update representation 70 within image 60, to show its true position, without the necessity of actually acquiring additional X-ray images. Nonetheless, a surgeon using system 30 will generally operate fluoroscope 54 from time to time to acquire additional images as the needle is being inserted, and particularly when the tip of the needle is approaching a potential danger zone, such as the spinal column.

Further preferably, controls 50 may be used to program a desired course 72, marked by a dash-dot line in FIG. 3, that needle 36 is to follow into intervertebral space 34. Course 72 is programmed, for example, by indicating to computer 48 an entry point 74 and a terminal point 76 for insertion of the needle. These data are then displayed on image 60 to aid in alignment of guide 38 with course 72, and to track the progress of needle 36 along the course. Preferably, computer 48 issues an audible alarm if needle 36 deviates from course 72 by more than a predetermined tolerance and/or cues the surgeon as to the required course correction. Additionally or alternatively, if guide 38 is suitably automated and connected to computer 48, the computer may automatically control and adjust the guide to position needle 36 at an appropriate angle.

Image 60 may be renewed as desired, by acquisition of new images by fluoroscope 54. Preferably, after each such acquisition, computer 48 repeats the image processing steps described above, in order to re-register the image-based and signal-based coordinates of element 20 and needle 36. Image 60 should be renewed, in particular, if the signal-based coordinates of device 24 change, for example due to movement of patient 32. Similarly, if a new image is acquired from a different view angle or having a different scale from the previous image, the coordinates are preferably re-registered and transformed.

Figure 4:
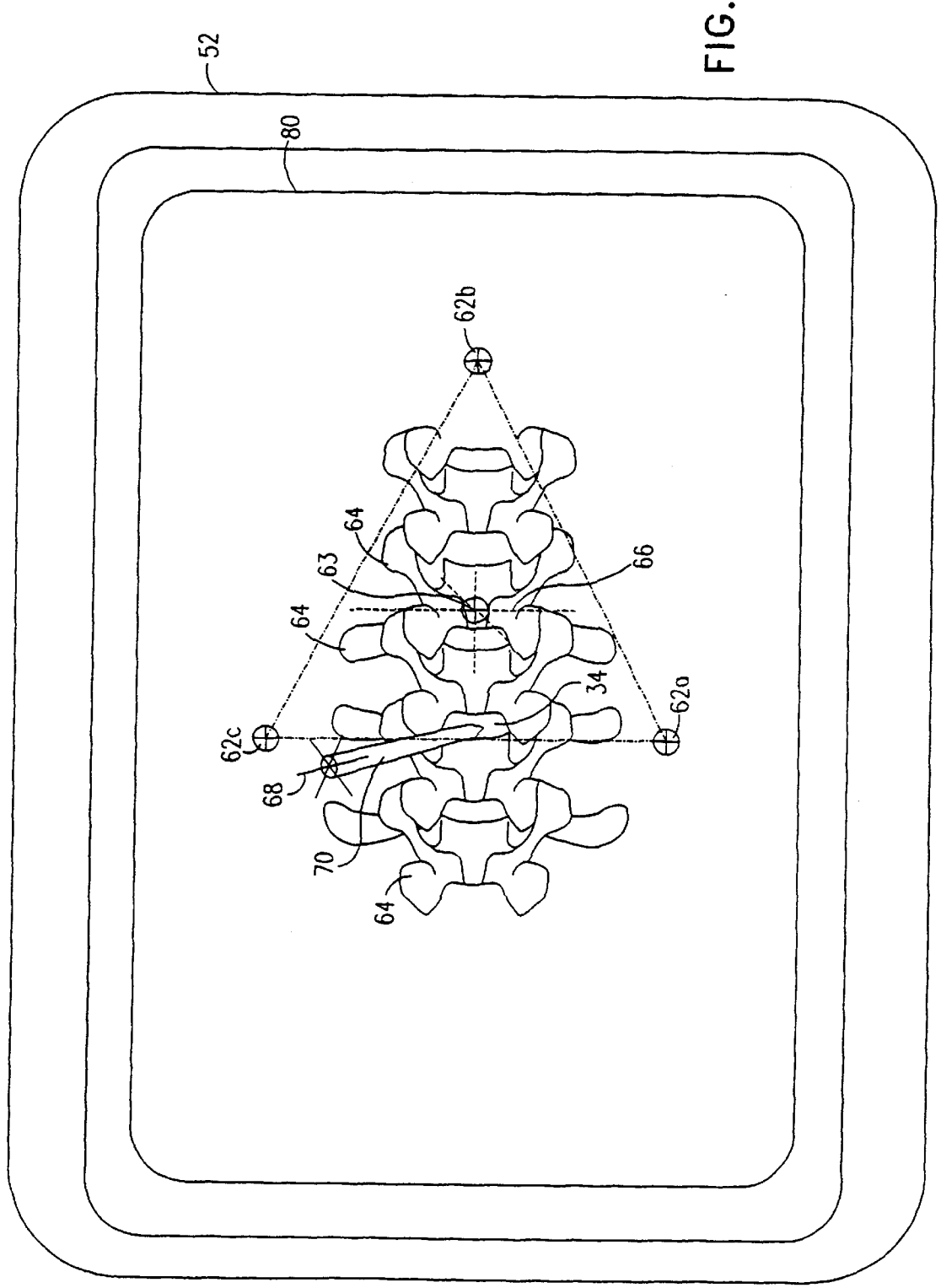
FIG. 4 is a schematic representation of an anterior-posterior X-ray image, similarly including elements of the system of FIG. 2, in accordance with a preferred embodiment of the present invention.

FIG. 4 illustrates schematically an anterior-posterior image 80 acquired by fluoroscope 54, after suitably rotating the tube and screen 56 by approximately 90° around patient 32 from the position shown in FIG. 2. The image is processed to locate points 62a, 62b, 62c and 63 and to display respective position and orientation axes 66 and 68 of devices 24 and 40, along with representation 70 of needle 36, as described above. As needle 36 is viewed along a generally longitudinal direction in image 80, representation 70 is foreshortened. The surgeon operating system 30 may, however, choose any convenient view angles, including oblique views.

Figure 5:
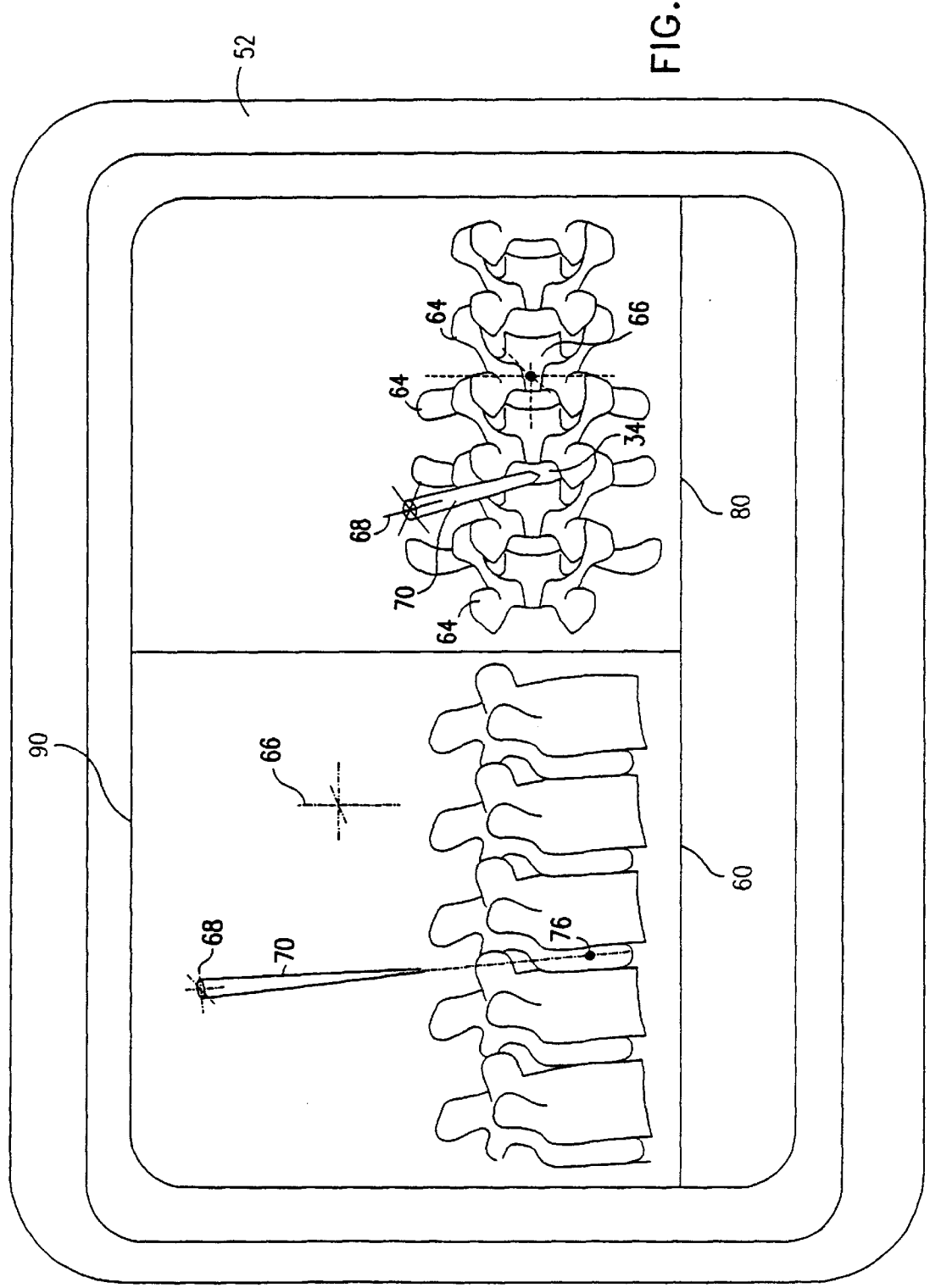
FIG. 5 is a schematic representation of a split-screen fluoroscopic video image, illustrating simultaneous dual-plane imaging, in accordance with a preferred embodiment of the present invention.

FIG. 5 illustrates schematically a split-screen display 90 showing the data generated by system 30, in accordance with a preferred embodiment of the present invention. Preferably, image 80 is displayed alongside image 60 within display 90, and the position of representation 70 in both images is updated, as described above, so that the progress of needle 36 entering space 34 can be visualized in both lateral and anterior-posterior views simultaneously. It will be appreciated that the present invention makes it possible to observe such dual-plane, dynamic images, without the need for repeatedly acquiring new images in both or even one of the planes. New images in either of the planes or in another, different plane may be acquired as often as desired, however, and display 90 will be updated accordingly.

In some preferred embodiments of the present invention, X-ray images 60 and/or 80 are registered with previously-acquired CT images of the body of patient 32. Before acquiring the CT images, reference element 20 is fixed to the body in a desired position, as shown in FIG. 2, for example, so that fiducial marks 22 and 23 on the element appear in the CT images. Element 20 remains fixed to the body in this position during the surgical procedure. The image-derived coordinates of the fiducial marks in the X-ray images are compared with corresponding image-derived coordinates in the CT images, in order to register the X-ray and CT images.

Preferably, based on this image registration, the CT images are rotated and/or scaled, as is known in the art, so as to align the CT images with one or both of X-ray images 60 and 80. Furthermore, three-dimensional CT image information, rotated and/or scaled in this manner, may be projected onto the plane of one or both X-ray images and superimposed on the X-ray images or displayed alongside them. Additionally or alternatively, the coordinates of tool 36 and/or an image of the tool may be displayed on an appropriate CT image.

Although the above preferred embodiments have been described generally with reference to certain types of position and orientation sensing devices 24 and 40, it will be appreciated that the principles of the present invention may be applied using any other suitable types of position and orientation sensors, as are known in the art.

Figure 6:
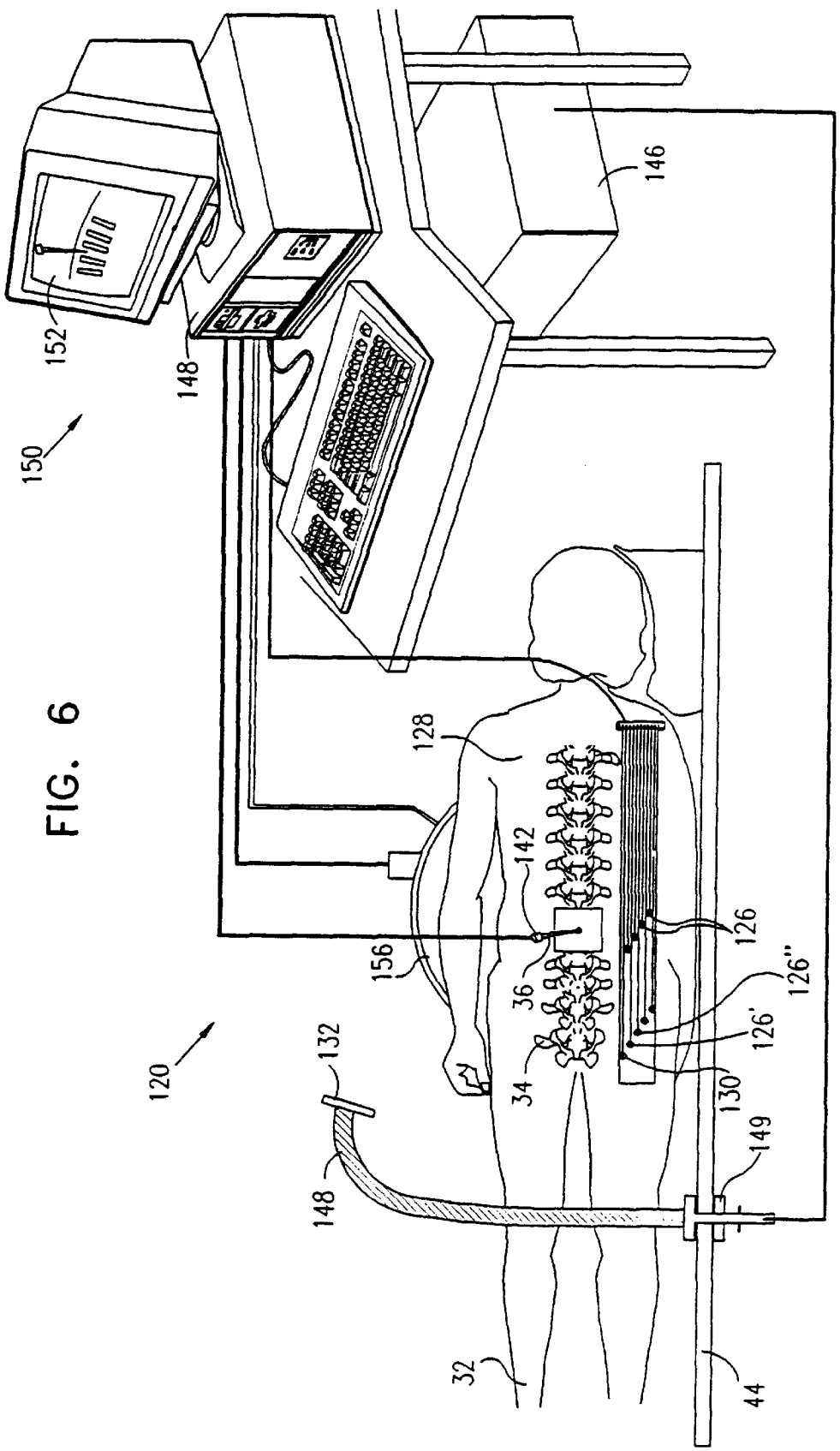
FIG. 6 is a schematic illustration of a surgical system, in accordance with another preferred embodiment of the present invention.

FIG. 6 is a schematic view of a system 120 for spinal surgery, in accordance with another preferred embodiment of the present invention. As in FIG. 2, patient 32 is lying on a bed 44 in preparation for back surgery. A plurality of reference sensors 126 are attached to the back 128 of patient 32, preferably using a suitable medical adhesive. Each sensor 126 preferably comprises a fiducial mark 130, allowing easy recognition of sensors 126 in images of back 128. Preferably, fiducial marks 130 are embedded within, or placed on sensors 126. In order to register the position of a sensor 126 on an image of back 128, at least three marks 130 are used, preferably those marks associated with sensors neighboring the registered sensor. Alternatively, each sensor 126 is fixedly coupled to three fiducial marks attached to patient 32, such that there is a known relation between sensors 126 and marks 130. Further alternatively, a plurality of marks 130 are attached to back 128 at a sufficient density such that each sensor 126 has at least three marks 130 in its proximity, so as to allow registration of the position of sensor 126 relative to the image.

A surgical needle 36, with a sensor 142 mounted at a fixed position relative its tip, is inserted into back 128, for example, to aspirate a ruptured disc. A radiator 132, coupled to a position determining system 150, is maneuverably positioned in the vicinity of back 128, in order to transmit and/or receive magnetic fields to and/or from sensor 142 and determine the position of the tip of needle 36. Position determining system 150 is preferably as described above with reference to FIG. 2, and/or as described in U.S. Pat. Nos. 5,558,091, 5,391,199 or 5,443,489, or in International Patent Publications WO 94/04938 or WO 96/05768, which are incorporated herein by reference.

Preferably, position determining system 150 is coupled with an imaging device 156, such as fluoroscope 54 described above, in order to register the positions of sensors 142 and 126 on an image visualized by the surgeon. It will be understood, however, that system 150, as described herein, may also be used together with other imaging devices, including MRI and CT, and/or other coupling methods may be used, for example, as described in PCT publication WO/08209 or in U.S. Pat. No. 5,383,454, which are incorporated herein by reference.

Figure 8:
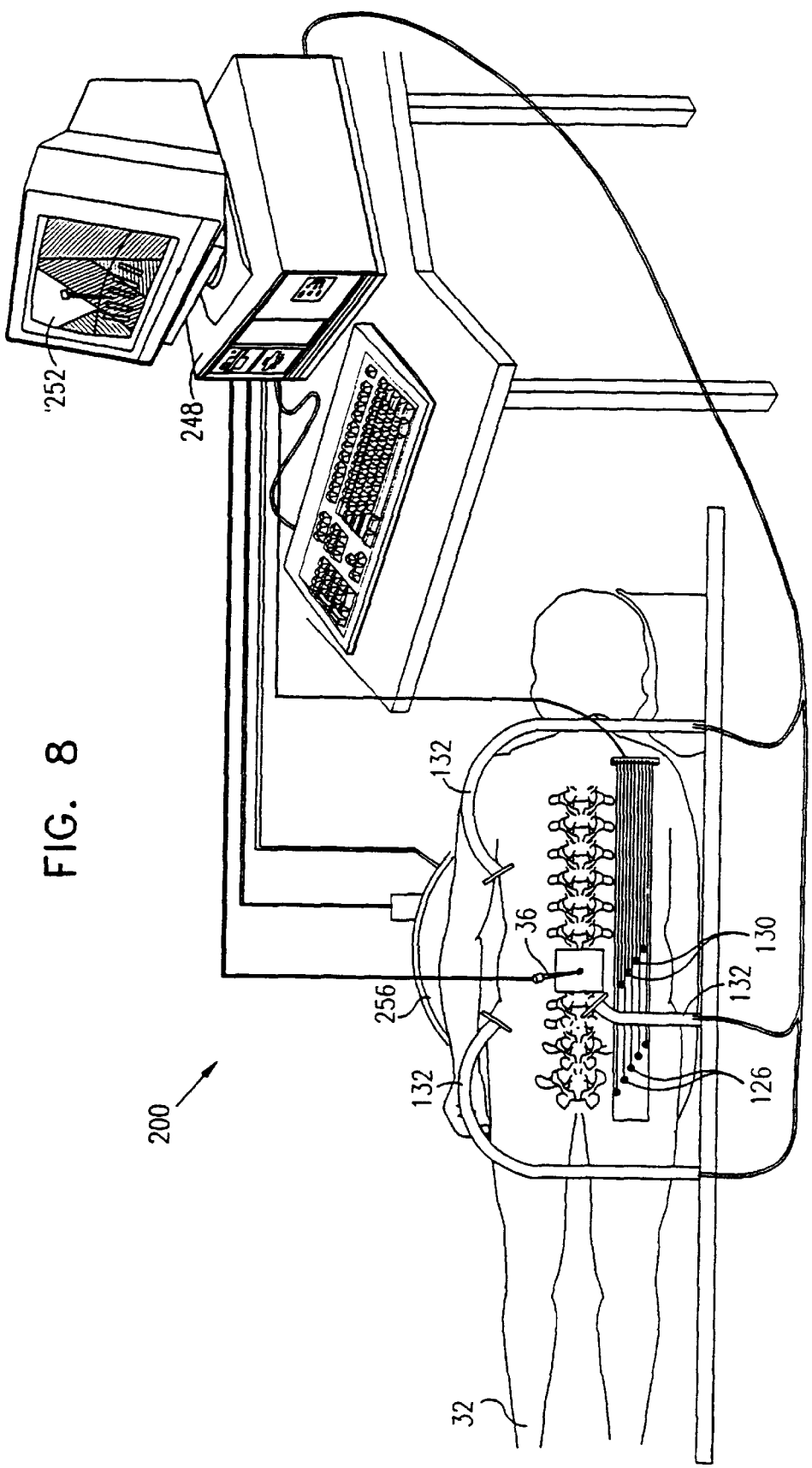
FIG. 8 is a schematic illustration of a surgical system, in accordance with still another preferred embodiment of the present invention.

Preferably, radiator 132 comprises one or more field transducers, preferably field transmitting coils of a small size. Preferably, radiator 132 comprises three coils, which are most preferably mutually substantially orthogonal. Alternatively or additionally, a plurality of radiators are used, as shown in FIG. 8, below. Preferably, a ferrite core is incorporated within each coil. The coils are preferably mounted on radiator 132 in a manner described in PCT/US97/02440, although any other suitable mounting setup may be used. Preferably, the coils of radiator 132 are driven at different frequencies or alternatively are time multiplexed or otherwise driven differently, so that the respective field generated by each of the coils can be distinguished from the fields of the other coils.

Preferably, radiator 132 is mounted on a goose neck 148 which is attached to bed 44 by a clamp 149. Alternatively, goose neck 148 may slide along a railing of bed 44. Further alternatively, radiator 132 may be mounted on any suitable mounting device allowing easy movement into and out of the vicinity of needle 36.

Sensors 126 are preferably placed near the vertebrae 34 of patient 32 at a suitable density. Preferably, for substantially every point in which sensor 142 may be positioned, at least one sensor 126 will be within a detection volume of radiator 132 which encompasses both sensor 126 and the point. The detection volume of radiator 132 is defined as the volume in which sensors 126 and 142 may be placed such that signals passed between radiator 132 and the sensors are strong enough to allow the location of the sensor to be determined to a predetermined accuracy and/or with a predetermined signal/noise ratio.

Figure 7:
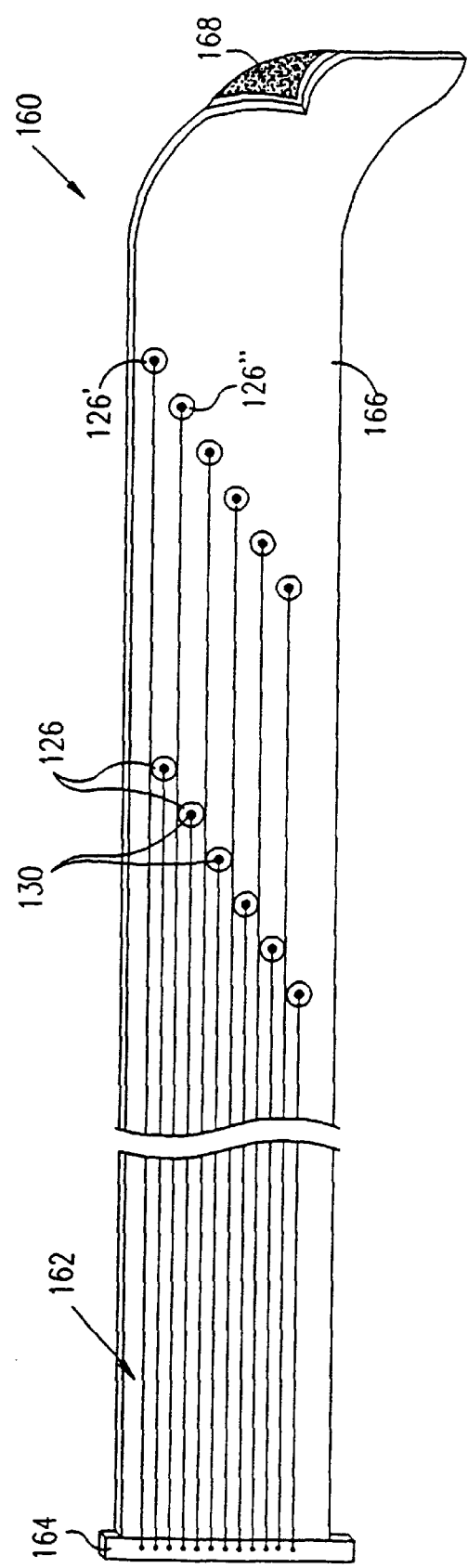
FIG. 7 is a perspective view of a reference sensor strap, in accordance with a preferred embodiment of the present invention.

FIG. 7 schematically shows a strap 160 holding reference sensors 126, in accordance with a preferred embodiment of the present invention. Strap 160 comprises a long strip of a cloth or other suitable material for fixed attachment to patient 32. Sensors 126 are embedded within strap 160 or are attached on an outer surface 166 of the strap. Fiducial marks 130 are fixedly positioned on strap 160 relative to sensors 126. Preferably, marks 130 are attached to sensors 126. A wire bus 162 connects sensors 126 along strap 160 to a standard plug connection 164 at an end of strap 160.

Preferably, strap 160 is produced in standard sizes and is supplied wound in a small bundle. In preparation for surgery, strap 160 is unwound onto patient 32. Preferably, an inner surface 168 of strap 160 has a medical adhesive which attaches strap 160 to patient 32. Alternatively, the adhesive is placed by a surgeon when strap 160 is unwound onto the patient.

In some medical procedures, more than one strap 160 may be used for position reference. Specifically, two straps 160 may be placed adjacent to an area which is to be operated on, at opposite sides of the area.

Preferably, reference sensors 126 comprise three-axis miniature coils such as described, for example in the above-mentioned PCT publication WO96/05768, or in PCT publications PCT/GB93/01736, WO97/24983 or WO94/04938, or in U.S. Pat. No. 5,391,199, all of which are incorporated herein by reference.

Before the surgery, position determining system 150 is calibrated, so that the determined positions of sensors 126 are registered on an image of patient 32 which includes images of fiducial marks 130. The determined positions of sensors 126 are registered on the image according to the image of their corresponding marks 130. Preferably, marks 130 are automatically identified on the image according to their shape or computed density. Alternatively or additionally, the surgeon indicates the locations of marks 130 on the image. Consequently, the positions of sensors 126 on the image are determined according to their known relation to marks 130.

Preferably, calibration also includes determining the positions of sensors 126 relative to one another. Preferably a large, long-range radiator is used to determine the relative positions of reference sensors 126. Alternatively, radiator 132 is used for calibration which is performed relative to one of reference sensors 126', which is chosen arbitrarily. Radiator 132 is positioned at an arbitrary point near reference sensor 126', and the positions of the adjacent sensors 126" are determined. Radiator 132 is then moved to determine the positions of another group of sensors 126 relative to those sensors whose positions were already determined. This procedure is repeated until substantially all the positions of sensors 126 are determined. Further alternatively, sensors 126 are at fixed positions relative to each other, and these positions are pre-stored in position determining system 150. During calibration it is only necessary to determine the position of one of sensors 126 and the positions of the rest of sensors 126 are calculated accordingly.

During surgery, radiator 132 is maneuvered as necessary into the proximity of needle 36 to provide accurate tracking, without interfering with the actions of medical staff performing the surgery. Radiator 132 continues to transmit magnetic fields, regardless of its position. Position determining system 150 measures the signals received at sensor 142 on needle 36, and in one or more of reference sensors 126 near the needle, and accordingly determines the needle's position and orientation. Position determining system 150 thus registers the position of needle 36 in a reference frame fixed to back 128, irrespective of the movement of radiator 132 or of patient 32, and displays an image or cursor corresponding to the needle position on fluoroscopic and/or CT or MRI images of the back, as described above.

Preferably, periodically at a suitable rate, such as every few seconds and/or every time radiator 132 is moved, position determining system 150 performs a procedure of assigning a current reference sensor 126, with respect to which the position of sensor 142 on needle 36 is determined. Radiator 132 transmits a test signal, which is preferably the same signal used for position determination. System 150 measures the signals received by each of reference sensors 126 responsive to the test signal. The sensor having the strongest received signal is defined as the currently assigned reference sensor. Alternatively, the currently assigned reference sensor is chosen to be the reference sensor 126 closest to radiator 132, based on a real-time image of patient 32.

FIG. 8 is a schematic illustration of a surgical system 200, in accordance with another preferred embodiment of the present invention. System 200 includes a plurality of radiators 132, which are used to determine the positions of sensors 126. Use of multiple sensors 126 allows use of small radiators 132, which do not require much space. Also, use of multiple radiators allows the detection volume of each radiator 132 to be decreased, and consequently increases the resolution of position determination performed using the radiators.

Preferably, radiators 132 are operated sequentially, so that fields transmitted by one radiator do not interfere with position determination using the other radiators. Alternatively, only one radiator is operated continuously at any given time. This radiator is chosen to be the radiator closest to needle 36. Further alternatively, the radiators generate fields of different frequencies which substantially do not interfere with each other. Preferably, assigning the current reference sensor 126 is performed independently for each radiator 132, i.e., each radiator has its own current reference sensor.

Preferably, system 200 includes a fluoroscope 256 which acquires images of patient 32 and fiducial marks 130. A computer 248 processes the resulting images and displays them on a display 252. Preferably, the images are processed according to positions determined using radiators 132.

Figure 9:
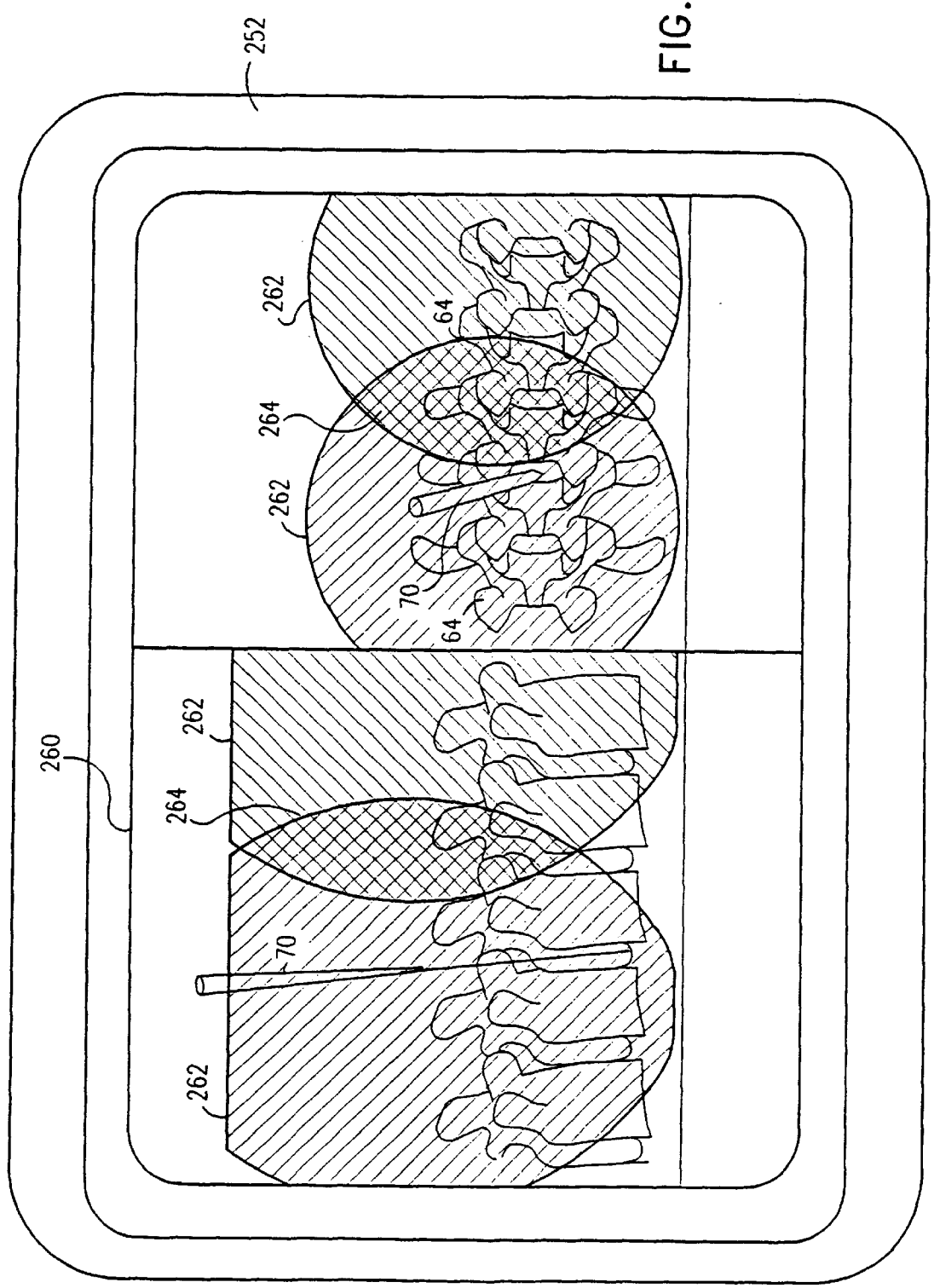
FIG. 9 is a schematic representation of an X-ray image, including elements of the system of FIG. 8, in accordance with a preferred embodiment of the present invention.

FIG. 9 is a schematic illustration of a fluoroscopic image 260, as displayed by display 252 following processing by computer 248, in accordance with a preferred embodiment of the present invention. Preferably, areas 262 included in the detection volume of radiators 132 are indicated on image 260. Preferably, the detection volume of each radiator 132 is indicated differently, so as to associate indicated areas 262 with respective radiators 132. For example, each radiator 132 may be painted a different color, and that color is used on image 260 to indicate the detection volume of the respective radiator. Preferably, areas included in two detection volumes, for example area 264, are marked accordingly.

During surgery the surgeon or an assistant preferably makes sure that desired areas are included within the detection volume of at least one radiator. When a desired area is not in the detection volume of any of radiators 132, the surgeon or assistant may move one of the radiators to a position in which it includes the desired area in its detection volume.

Preferably, the span of the detection volume of each radiator 132 is known by computer 248 before surgery, possibly as a function of a predetermined, maximum coordinate resolution, and according to the position of the radiator, its detection volume is indicated. Alternatively or additionally, the radiator transmits fields to reference sensors 126 and according to those which respond with a strong enough signal, the radiator position and/or detection volume is determined.

It will be appreciated that although preferred embodiments are described herein with reference to certain types of surgical procedures, for example, treatment of the intervertebral discs, the principles of the present invention may similarly be applied to procedures of other types, including head surgery, biopsies, and tube insertion.

Furthermore, although in the preferred embodiments described hereinabove, the radiators are described as transmitting magnetic fields, which are received by the position sensors, the principles of the present invention can similarly be applied in position determining systems in which the sensors transmit fields, and the radiators are replaced by receivers, as are known in the art. It will also be understood that other types of energy fields may be used in the position determination, as is known in the art, such as ultrasonic energy.

It will further be understood that the preferred embodiments described above are cited by way of example, and the full scope of the invention is limited only by the claims

What is claimed is:

1. A method for image guided surgery, comprising:
   placing a reference element, to which a reference coordinate sensing device is fixed, on the body of a patient, the reference coordinate sensing device generating signals used for determining position and orientation coordinates of the reference element;
   acquiring an image of the body, including the element, during the surgery;
   processing the image to determine image-based coordinates of the reference coordinate sensing device;
   receiving and processing signals from the reference coordinate sensing device to determine signal-based coordinates in the form of position and orientation coordinates thereof;
   registering the image-based and signal-based coordinates to determine a coordinate transformation therebetween;
   bringing a surgical tool having a tool coordinate sensing device into proximity with the body of the patient, the tool coordinate sensing device generating signals used for determining position and orientation coordinates of the tool;
   receiving and processing signals from the tool coordinate sensing device to determine signal-based coordinates in the form of position and orientation coordinates thereof;
   determining image-based coordinates of the tool by applying the coordinate transformation to the signal-based coordinates of the tool coordinate sensing device;
   programming a desired course that the tool is to follow in the body;
   displaying the desired course on the image;
   advancing the tool in the body along the displayed desired course; and
   tracking the progress of the advanced tool along the displayed desired course.

2. A method according to claim 1, wherein registering the coordinates to determine a coordinate transformation comprises determining an image scale factor.

3. A method according to claim 2, and comprising determining coordinates of an X-ray camera used to acquire an X-ray image, wherein determining the image scale factor comprises comparing the camera coordinates to the coordinates of the reference coordinate sensing device.

4. A method according to claim 1, wherein acquiring the image comprises acquiring a plurality of images from different view angles with respect to the body, and wherein displaying the image and registering the representation of the tool therein comprises registering a suitably-oriented representation of the tool in at least two of the plurality of images.

5. A method according to claim 1, further comprising indicating an entry point and a terminal point for insertion of the tool.

6. A method according to claim 5, and comprising displaying a linear course for the displayed desired course along which the tool is to be advanced.

7. A method according to claim 6, and comprising advancing the tool into the body and comparing coordinates of the tool to the linear course so as to detect a deviation of the tool from the course.

8. A method according to claim 5, further comprising issuing an alarm if the tool deviates from the displayed desired course.

9. A method according to claim 8, further comprising providing a predetermined tolerance for deviation of the tool from the displayed desired course and issuing the alarm when the tool deviates by more than the predetermined tolerance.

10. A method according to claim 1, further comprising automatically controlling the position of the tool.

11. A method according to claim 1, wherein the image acquired is by a fluoroscope.

12. A method according to claim 1, wherein the image acquired is by an MRI imaging device.

13. A method according to claim 1, wherein the image acquired is by a CT imaging device.

14. A method according to claim 1, including providing a plurality of reference coordinate sensing devices.

15. A method for performing image guided surgery on a body of a patient, the method comprising the steps of:
   providing at least one reference element having a position and orientation sensing device thereon on the body of the patient;
   acquiring an image of the body and the at least one reference element and determining image-based coordinates of the at least one reference element;
   providing at least one magnetic field radiator in proximity to the body of a patient;
   applying a magnetic field to the body of the patient with the at least one magnetic field radiator;
   establishing a frame of reference with the at least one magnetic field radiator and the at least one reference element;
   generating at least one signal with the position and orientation sensing device of the at least one reference element for determining position and orientation coordinates of the at least one reference element based on the applied magnetic field;
   registering the position and orientation coordinates with the image-based coordinates for the at least one reference element and determining a coordinate transformation therebetween;
   providing a tool having a tool position and orientation sensing device thereon;
   placing the tool within the frame of reference and generating at least one signal with the tool position and orientation sensing device for determining position and orientation coordinates of the tool;
   determining image-based coordinates for the tool by applying the coordinate transformation to the tool position and orientation coordinates;
   superimposing a representation of the tool on the image; and performing a procedure with the tool and tracking the tool with the representation on the image.

16. The method according to claim 15, further comprising including at least one sensor coil with the position and orientation sensing device of the at least one reference element.

17. The method according to claim 16, further comprising including at least one sensor coil with the tool position and orientation sensing device.

18. The method according to claim 17, further comprising including at least one generator coil with the at least one magnetic field generator.

19. The method according to claim 18, further comprising determining three dimensional position coordinates and two dimensional angular azimuth and elevation coordinates with the tool position and orientation sensing device.

20. The method according to claim 19, further comprising determining roll angle coordinates with the tool position and orientation sensing device.

21. The method according to claim 15, further comprising displaying the image on a display.

22. The method according to claim 21, further comprising performing a surgical procedure with the tool.

23. The method according to claim 22, further comprising performing a biopsy procedure with the tool.

24. The method according to claim 21, further comprising acquiring a fluoroscope image of the body.

25. The method according to claim 21, further comprising acquiring an MRI image of the body.

26. The method according to claim 21, further comprising acquiring an X-Ray image of the body.

27. The method according to claim 21, further comprising acquiring a CT image of the body.

28. The method according to claim 21, further comprising using the at least one reference element as a fiducial marker.

* * * * *